United States Patent
Paul et al.

[19]

[11] Patent Number: 6,060,638
[45] Date of Patent: *May 9, 2000

[54] MATCHED PERMEABILITY LINER/ ABSORBENT STRUCTURE SYSTEM FOR ABSORBENT ARTICLES AND THE LIKE

[75] Inventors: Susan Carol Paul; Philip Anthony Sasse; David George Crowther, all of Alpharetta; Eric Mitchell Johns, Roswell, all of Ga.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/740,767

[22] Filed: Nov. 1, 1996

Related U.S. Application Data

[60] Provisional application No. 60/009,171, Dec. 22, 1995.

[51] Int. Cl.[7] .................................................... A61F 13/15
[52] U.S. Cl. ........................................... 604/378; 604/367
[58] Field of Search .................................. 604/358, 367, 604/364, 374, 378, 385.1

[56] References Cited

U.S. PATENT DOCUMENTS

| H1377 | 11/1994 | Perry | 604/385.1 |
| H1511 | 12/1995 | Chappell et al. | 604/383 |

(List continued on next page.)

FOREIGN PATENT DOCUMENTS

| 2147685 | 2/1996 | Canada . |
| 0 343 941 | 11/1989 | European Pat. Off. . |

(List continued on next page.)

OTHER PUBLICATIONS

Research Disclosure 37421, "Thermally Bonded Absorbent Structures Having Discrete, Stepped Density Zones in the Z–Dimension," Jun. 1995, Inventor—Anonymous.

(List continued on next page.)

*Primary Examiner*—Corrine McDermott
*Assistant Examiner*—David J. Cho
*Attorney, Agent, or Firm*—Nicholas Leach; James B. Robinson

[57] ABSTRACT

The present invention is directed to a matched permeability liner/absorbent structure system, suitable for use in absorbent articles, in which the permeability of the bodyside liner is correlated with the permeability of the subjacent layer of the absorbent structure, such as a surge layer. The inventors have observed that by appropriately matching the permeability of the liner material to the permeability of the subjacent layer, liquid intake performance of the liner and subjacent layer materials can exceed liquid intake performance of the subjacent layer material alone. Thus, in accordance with an embodiment of the present invention, the permeability of the bodyside liner is set within a specified range of that of the subjacent layer such that the liner/subjacent layer liquid intake performance is improved. In accordance with another embodiment of the present invention, the permeability of the bodyside liner is matched to or correlated with the permeability of the subjacent layer such that the liner/subjacent layer liquid intake performance is improved at least about 50 percent over the liquid intake performance of the subjacent layer alone. In accordance with yet another embodiment of the present invention, the permeability of the liner material is matched to or correlated with the permeability of the subjacent layer such that liquid intake performance of the liner/subjacent layer combination is improved at least about 65 percent over the liquid intake performance of the subjacent layer alone. As disclosed herein, by properly selecting the permeability of the liner material, as compared with the permeability of the subjacent layer material, the liquid intake rate of the liner material not only does not limit or inhibit liquid intake into the subjacent layer and underlying components of the absorbent structure, but provides an unexpected increase in liquid intake performance over that of the subjacent layer alone. The bodyside liner and subjacent layer can suitably be formed of fibrous nonwoven webs.

19 Claims, 3 Drawing Sheets

6,060,638

U.S. PATENT DOCUMENTS

| | | | |
|---|---|---|---|
| 3,276,944 | 10/1966 | Levy | 161/150 |
| 3,307,545 | 3/1967 | Surowitz | 128/156 |
| 3,338,992 | 8/1967 | Kinney | 264/24 |
| 3,341,394 | 9/1967 | Kinney | 161/72 |
| 3,423,266 | 1/1969 | Davies et al. | 156/167 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,683,486 | 8/1972 | Rope et al. | 29/428 |
| 3,692,618 | 9/1972 | Dorschner et al. | 161/72 |
| 3,744,627 | 7/1973 | Rope et al. | 206/80 A |
| 3,802,817 | 4/1974 | Matsuki et al. | 425/66 |
| 3,855,046 | 12/1974 | Hansen et al. | 161/150 |
| 3,929,135 | 12/1975 | Thompson | 128/287 |
| 4,041,951 | 8/1977 | Sanford | 128/287 |
| 4,187,210 | 2/1980 | Howard, Jr. | 260/42.14 |
| 4,340,563 | 7/1982 | Appel et al. | 264/518 |
| 4,342,314 | 8/1982 | Radel et al. | 128/287 |
| 4,350,655 | 9/1982 | Hoge | 264/145 |
| 4,397,644 | 8/1983 | Matthews et al. | 604/378 |
| 4,413,032 | 11/1983 | Hartmann et al. | 428/288 |
| 4,434,258 | 2/1984 | Schumacher et al | 524/13 |
| 4,480,000 | 10/1984 | Watanabe et al. | 428/284 |
| 4,500,315 | 2/1985 | Pieniak et al. | 604/379 |
| 4,531,945 | 7/1985 | Allison | 604/378 |
| 4,537,590 | 8/1985 | Pieniak et al. | 604/379 |
| 4,539,256 | 9/1985 | Shipman | 428/315.5 |
| 4,540,414 | 9/1985 | Wishman | 604/378 |
| 4,573,988 | 3/1986 | Pieniak et al. | 604/379 |
| 4,578,070 | 3/1986 | Hoitman | 604/378 |
| 4,636,209 | 1/1987 | Lassen | 604/378 |
| 4,637,819 | 1/1987 | Quellette et al. | 604/369 |
| 4,650,479 | 3/1987 | Insley | 604/358 |
| 4,670,011 | 6/1987 | Mesek | 604/378 |
| 4,673,402 | 6/1987 | Weisman et al. | 604/368 |
| 4,681,577 | 7/1987 | Stern et al. | 604/378 |
| 4,685,914 | 8/1987 | Holtman | 604/368 |
| 4,699,619 | 10/1987 | Bernardin | 604/378 |
| 4,704,116 | 11/1987 | Enloe | 604/385 A |
| 4,723,953 | 2/1988 | Rosenbaum et al. | 604/369 |
| 4,755,178 | 7/1988 | Insley et al. | 604/367 |
| 4,762,520 | 8/1988 | Wallstrom | 604/366 |
| 4,777,073 | 10/1988 | Sheth | 428/155 |
| 4,798,603 | 1/1989 | Meyer et al. | 604/378 |
| 4,814,124 | 3/1989 | Aoyama et al. | 264/41 |
| 4,830,904 | 5/1989 | Gessner et al. | 428/219 |
| 4,834,735 | 5/1989 | Alemany et al. | 604/378 |
| 4,842,594 | 6/1989 | Ness | 604/368 |
| 4,879,078 | 11/1989 | Antoon, Jr. | 264/41 |
| 4,880,419 | 11/1989 | Ness | 604/368 |
| 4,892,534 | 1/1990 | Datta et al. | 604/370 |
| 4,904,249 | 2/1990 | Miller et al. | 604/378 |
| 4,908,026 | 3/1990 | Sukiennik et al. | 604/368 |
| 4,929,303 | 5/1990 | Sheth | 156/209 |
| 4,935,022 | 6/1990 | Lash et al. | 604/368 |
| 4,938,756 | 7/1990 | Salek | 604/368 |
| 4,950,264 | 8/1990 | Osborn, III | 604/385.1 |
| 4,988,344 | 1/1991 | Reising et al. | 604/368 |
| 4,988,345 | 1/1991 | Reising | 604/368 |
| 4,994,037 | 2/1991 | Bernardin | 604/368 |
| 5,004,465 | 4/1991 | Ternstrom et al. | 604/385.1 |
| 5,009,653 | 4/1991 | Osborn, III | 604/385.1 |
| 5,030,229 | 7/1991 | Yang | 604/385.1 |
| 5,037,409 | 8/1991 | Chen et al. | 604/358 |
| 5,043,206 | 8/1991 | Ternström | 428/218 |
| 5,047,023 | 9/1991 | Berg | 604/368 |
| 5,062,839 | 11/1991 | Anderson | 604/385.1 |
| 5,124,197 | 6/1992 | Bernardin et al. | 428/284 |
| 5,134,007 | 7/1992 | Reising et al. | 428/78 |
| 5,147,345 | 9/1992 | Young et al. | 604/378 |
| 5,171,391 | 12/1992 | Chmielewski et al. | 156/229 |
| 5,176,668 | 1/1993 | Bernardin | 604/368 |
| 5,176,953 | 1/1993 | Jacoby et al. | 428/315.5 |
| 5,188,624 | 2/1993 | Young, Sr. et al. | 604/378 |
| 5,192,606 | 3/1993 | Proxmire et al. | 428/284 |
| 5,200,248 | 4/1993 | Thompson et al. | 428/131 |
| 5,217,445 | 6/1993 | Young et al. | 604/381 |
| 5,236,427 | 8/1993 | Hamajima et al. | 604/378 |
| 5,242,435 | 9/1993 | Murji et al. | 604/374 |
| 5,248,309 | 9/1993 | Serbiak et al. | 604/368 |
| 5,257,982 | 11/1993 | Cohen et al. | 604/378 |
| 5,281,207 | 1/1994 | Chmielewski et al. | 604/378 |
| 5,281,208 | 1/1994 | Thompson et al. | 604/378 |
| 5,294,478 | 3/1994 | Wanek et al. | 428/218 |
| 5,300,054 | 4/1994 | Feist et al. | 604/378 |
| 5,304,161 | 4/1994 | Noel et al. | 604/378 |
| 5,318,554 | 6/1994 | Young et al. | 604/378 |
| 5,330,457 | 7/1994 | Cohen | 604/378 |
| 5,334,176 | 8/1994 | Buenger et al. | 604/367 |
| 5,334,177 | 8/1994 | Cohen | 604/378 |
| 5,342,334 | 8/1994 | Thompson et al. | 604/366 |
| 5,342,336 | 8/1994 | Meirowitz et al. | 604/378 |
| 5,348,547 | 9/1994 | Payne et al. | 604/378 |
| 5,350,370 | 9/1994 | Jackson et al. | 604/367 |
| 5,353,485 | 10/1994 | Billgren et al. | 28/104 |
| 5,356,405 | 10/1994 | Thompson et al. | 604/384 |
| 5,360,420 | 11/1994 | Cook et al. | 604/378 |
| 5,364,382 | 11/1994 | Latimer et al. | 604/378 |
| 5,366,451 | 11/1994 | Levesque | 604/378 |
| 5,368,926 | 11/1994 | Thompson et al. | 428/284 |
| 5,382,245 | 1/1995 | Thompson et al. | 604/367 |
| 5,401,267 | 3/1995 | Couture-Dorschner | 604/384 |
| 5,415,640 | 5/1995 | Kirby et al. | 604/383 |
| 5,418,045 | 5/1995 | Pike et al. | 428/198 |
| 5,423,787 | 6/1995 | Kjellberg | 604/368 |
| 5,429,629 | 7/1995 | Latimer et al. | 604/378 |
| 5,439,458 | 8/1995 | Noel et al. | 604/378 |
| 5,456,982 | 10/1995 | Hansen et al. | 428/370 |
| 5,460,622 | 10/1995 | Dragoo et al. | 604/378 |
| 5,466,232 | 11/1995 | Cadieux et al. | 604/378 |
| 5,466,513 | 11/1995 | Wanek et al. | 428/218 |
| 5,486,166 | 1/1996 | Bishop et al. | 604/366 |
| 5,486,167 | 1/1996 | Dragoo et al. | 604/384 |
| 5,487,736 | 1/1996 | Van Phan | 604/368 |
| 5,490,846 | 2/1996 | Ellis et al. | 604/366 |
| 5,505,719 | 4/1996 | Cohen et al. | 604/372 |
| 5,509,915 | 4/1996 | Hanson et al. | 604/378 |
| 5,514,105 | 5/1996 | Goodman, Jr. et al. | 604/370 |
| 5,514,120 | 5/1996 | Johnston et al. | 604/378 |
| 5,525,407 | 6/1996 | Yang | 428/218 |
| 5,527,300 | 6/1996 | Sauer | 604/378 |
| 5,531,728 | 7/1996 | Lash | 604/378 |
| 5,536,264 | 7/1996 | Hsueh et al. | 604/368 |
| 5,540,979 | 7/1996 | Yahiaoui et al. | 428/212 |
| 5,549,589 | 8/1996 | Horney et al. | 604/366 |
| 5,556,392 | 9/1996 | Koczab | 604/378 |
| 5,562,646 | 10/1996 | Goldman et al. | 604/368 |
| 5,562,650 | 10/1996 | Everett et al. | 604/378 |
| 5,569,226 | 10/1996 | Cohen et al. | 604/378 |
| 5,599,335 | 2/1997 | Goldman et al. | 604/368 |
| 5,601,542 | 2/1997 | Glaug et al. | 604/385.2 |
| 5,607,414 | 3/1997 | Richards et al. | 604/378 |
| 5,611,981 | 3/1997 | Phillips et al. | 264/130 |
| 5,628,736 | 5/1997 | Thompson | 604/366 |
| 5,641,441 | 6/1997 | Yang | 264/113 |
| 5,643,238 | 7/1997 | Baker | 604/368 |
| 5,647,862 | 7/1997 | Osborn, III et al. | 604/378 |
| 5,649,916 | 7/1997 | DiPalma et al. | 604/378 |
| 5,658,268 | 8/1997 | Johns et al. | 604/361 |
| 5,665,082 | 9/1997 | Boulanger | 604/365 |

FOREIGN PATENT DOCUMENTS

| | | |
|---|---|---|
| 0 469 591 | 2/1992 | European Pat. Off. . |
| 0 532 005 | 3/1993 | European Pat. Off. . |
| 0 539 703 | 5/1993 | European Pat. Off. . |
| 0 640 330 | 3/1995 | European Pat. Off. . |
| 0 682 930 | 11/1995 | European Pat. Off. . |
| 0 719 530 | 7/1996 | European Pat. Off. . |
| 8164160 | 6/1996 | Japan . |
| 8164163 | 6/1996 | Japan . |
| 8299385 | 11/1996 | Japan . |
| 8317939 | 12/1996 | Japan . |
| 9000562 | 1/1997 | Japan . |
| 9117471 | 5/1997 | Japan . |
| 2 269 109 | 2/1994 | United Kingdom . |
| 2 295 321 | 5/1996 | United Kingdom . |
| 90/12130 | 10/1990 | WIPO . |
| 91/11978 | 8/1991 | WIPO . |
| 92/11830 | 7/1992 | WIPO . |
| 93/15702 | 8/1993 | WIPO . |
| 94/12713 | 6/1994 | WIPO . |
| 94/29506 | 12/1994 | WIPO . |
| 95/00183 | 1/1995 | WIPO . |
| 95/01147 | 1/1995 | WIPO . |
| 95/13042 | 5/1995 | WIPO . |
| 95/25495 | 9/1995 | WIPO . |
| 95/35081 | 12/1995 | WIPO . |
| 96/01608 | 1/1996 | WIPO . |
| 96/03947 | 2/1996 | WIPO . |
| 96/12460 | 5/1996 | WIPO . |
| 96/20667 | 7/1996 | WIPO . |
| 96/41045 | 12/1996 | WIPO . |
| 97/11660 | 4/1997 | WIPO . |
| 97/13909 | 4/1997 | WIPO . |
| 9723182 | 7/1997 | WIPO . |

OTHER PUBLICATIONS

Bernard Miller, David Clark, "Liquid Transport Through Fabrics; Wetting and Steady–State Flow," Sep. 13, 1977, pp. 150–155, Textile Research Journal.

MATCHED PERMEABILITY LINER/ABSORBENT STRUCTURE SYSTEM FOR ABSORBENT ARTICLES AND THE LIKE

This application claims priority from U.S. Provisional Application No. 60/009,171, filed Dec. 22, 1995.

FIELD OF INVENTION

The present invention relates to adapting the functionality of nonwoven and other materials, suitable for use as a bodyside liner of an absorbent article, to enhance the liquid intake performance of such absorbent article. More specifically, this invention relates to matching the permeability of the liner within a specified range of the permeability of a surge or other subjacent layer of an absorbent structure of the absorbent article in order to improve liquid intake performance of such absorbent article.

BACKGROUND OF THE INVENTION

Absorbent articles, particularly personal care absorbent articles, include diapers, training pants, feminine hygiene products such as sanitary napkins, incontinence devices and the like. Disposable absorbent articles are designed to absorb and contain body exudates. Such disposable products generally are single-use items which are discarded after a relatively short period of use—usually a period of hours—and are not intended to be washed and reused. Such articles usually are placed against or in proximity to the wearer's body to absorb and contain various exudates discharged from the body. All of these products typically include a liquid permeable bodyside liner or cover, a liquid impermeable outer cover or backsheet, and an absorbent structure disposed between the bodyside liner and outer cover. The absorbent structure may include a surge layer subjacent to and in liquid communicating contact with the bodyside liner, and an absorbent core formed of a blend or mixture cellulosic pulp fluff fibers and absorbent gelling particles subjacent to and in liquid communicating contact with the surge layer.

Desirably, personal care absorbent articles exhibit low leakage from the product and a dry feel for the wearer. An absorbent garment, such as a diaper, may leak from the leg or front or back waist areas. Leakage can result from a variety of performance deficiencies in the design of the product, or individual materials within the product. One cause of such leakage from an absorbent product is an insufficient rate of liquid intake into the absorbent core, which functions to absorb and retain body exudates.

It has been found that urination can occur at rates as high as 15 to 20 milliliters per second and at velocities as high as 280 centimeters per second. Therefore, the liquid intake of a given absorbent product, and particularly the liner and surge materials forming the absorbent product, must attempt to meet or exceed the expected liquid delivery rate into the absorbent product. The inability of the absorbent product to rapidly uptake liquid can result in excessive pooling of liquid on the body-facing surface of the bodyside liner before the liquid is taken up by the absorbent structure. Such pooled liquid can wet the wearer's skin and can leak from leg or waist openings of the absorbent article, causing discomfort, potential skin health problems, as well as soiling of the outer clothing or bedding of the wearer.

Various approaches have been taken to reduce or eliminate leakage from personal care absorbent articles. For example, physical barriers, such as elasticized leg openings and elasticized containment flaps, have been incorporated into such absorbent products. The amount and configuration of absorbent material in the zone of the absorbent structure in which liquid surges typically occur (sometimes referred to as a target zone) also have been modified.

Other approaches to improving overall liquid intake of absorbent articles have focused on the bodyside liner and its capacity to rapidly pass liquid to the absorbent structure of the absorbent article. Nonwoven materials, including bonded carded webs and spunbond webs, have been widely used as bodyside liners. Such nonwoven materials generally are intended to be sufficiently open and/or porous to allow liquid to pass through rapidly, while also functioning to keep the wearers skin separate from the wetted absorbent underlying the liner. Attempts to improve the liquid intake of liner materials have included, for example, aperturing the liner material, treating the fibers forming the liner material with surfactants to enhance the wettability of the liner, and altering the durability of such surfactants.

Yet another approach has been to introduce one or more additional layers of material, typically between the bodyside liner and absorbent core, to enhance the liquid intake performance of the absorbent product and to provide separation between the absorbent core and the bodyside liner adjacent the wearer's skin. Such additional layer or layers, commonly referred to as a surge layer, can suitably be formed of thick, lofty nonwoven materials. Surge layers, particularly high loft, high bulk, compression resistant fibrous structures, provide a temporary retention or absorption function for liquid not yet absorbed into the absorbent core, which tends to reduce fluid flowback or wetback from the absorbent core to the liner.

Notwithstanding the foregoing, the need exists for improvements in the liquid intake performance of liner materials employed in absorbent articles. In particular, there is a need for liner materials that can provide improved handling of liquid surges. The present invention provides a bodyside liner/absorbent structure system that provides for such improved liquid uptake when used in absorbent articles.

SUMMARY OF THE INVENTION

The present invention is directed to a matched permeability liner/absorbent structure system, suitable for use in absorbent articles, in which the permeability of the bodyside liner is correlated with the permeability of the subjacent layer of the absorbent structure, such as a surge layer. By appropriately matching the permeability of the liner material to the permeability of the subjacent layer, liquid intake performance of the liner and subjacent layer materials can exceed liquid intake performance of the subjacent layer material alone. Thus, in accordance with an embodiment of the present invention, the permeability of the bodyside liner is set within a specified range of that of the subjacent layer to provide enhanced liner/subjacent layer liquid intake performance. In accordance with another embodiment of the present invention, the permeability of the bodyside liner is matched to or correlated with the permeability of the subjacent layer such that the liner/subjacent layer liquid intake performance is improved at least about 50 percent over the liquid intake performance of the subjacent layer alone. In accordance with yet another embodiment of the present invention, the permeability of the liner material is matched to or correlated with the permeability of the subjacent layer such that liquid intake performance of the liner/subjacent layer combination is improved at least about 65 percent over the liquid intake performance of the subjacent layer alone. In accordance with the teachings herein, by properly selecting the permeability of the liner material, as compared with the permeability of the subjacent layer material, the liquid intake rate of the liner material not only does not limit or inhibit liquid intake into the subjacent layer and underlying components of the absorbent structure, but provides an unexpected increase in liquid intake performance over that of the subjacent layer alone. The bodyside liner and subjacent layer of the present invention can suitably be formed of fibrous nonwoven webs.

DETAILED DESCRIPTION OF THE INVENTION

The present invention generally relates to adapting the functionality of bodyside liner materials for absorbent articles in order to improve liquid intake into such absorbent articles. More specifically, this invention relates to matching the permeability of a bodyside liner material with the permeability of the underlying or subjacent layer of the absorbent structure, such as a surge layer, in order to enhance liquid intake performance.

For purposes of illustration only, the present invention will be described separately and in conjunction with its use with personal care absorbent articles. As such, the invention should not be limited to these specific uses, as it is instead intended that the present invention be used in all applications in which such liquid permeable and liquid absorbing materials can be employed, including, without limitation, surgical bandages and sponges, wipers and the like.

As used herein, the terms "layer" or "web" when used in the singular can have the dual meaning of a single element or a plurality of elements. As used herein, the terms "nonwoven layer" and "nonwoven web" mean a web having a structure of individual fibers or filaments which are interlaid, but not in an identifiable manner as in a knitted fabric. Commercially available thermoplastic polymeric materials can be employed advantageously in making the fibers from which nonwoven webs are formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specifically limited, the term "polymer" shall include all possible geometric configurations of the material, including, without limitation, isotactic, syndiotactic and random symmetries. As used herein, the terms "thermoplastic polymer" or "thermoplastic polymeric material" refer to a long-chain polymer that softens when exposed to heat and returns to its original state when cooled to ambient temperature. Exemplary thermoplastic materials include, without limitation, poly(vinyl chloride)s, polyesters, polyamides, polyfluorocarbons, polyolefins, polyurethanes, polystyrenes, poly(vinyl alcohol)s, caprolactams, and copolymers of the foregoing. The fibers used in making such nonwoven webs may have any suitable morphology and may include hollow or solid fibers, straight or crimped fibers, bicomponent, multicomponent, biconstituent or multiconstituent fibers, and blends or mixes of such fibers, as are well known in the art.

Figure 1:
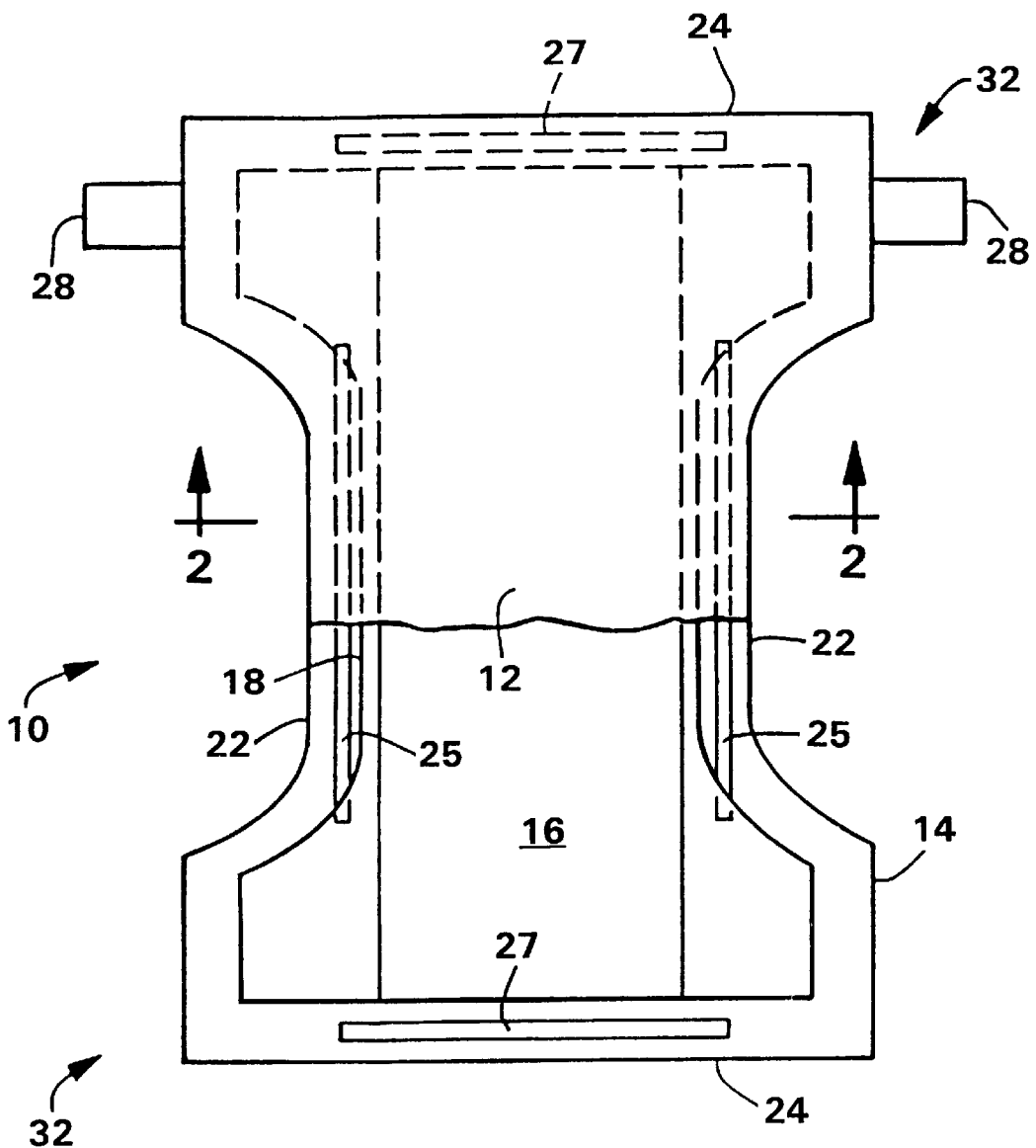
FIG. 1 is a partially cut away, top plan view of a disposable diaper including the liner/absorbent structure system of the present invention.

Referring to FIG. 1, a diaper 10 is shown, which, as is typical for most personal care absorbent articles, includes a liquid permeable topsheet or bodyside liner 12, a substantially liquid impermeable backsheet or outer cover 14 and an absorbent structure 20 positioned between liner 12 and outer cover 14. Liner 12 forms a body-facing surface which is compliant, soft-feeling and non-irritating to the wearer's skin. Liner 12 further serves to isolate the wearer's skin from the liquids held in absorbent structure 20. Various materials can be used in forming the bodyside liner 12 of the present invention, including apertured plastic films, woven fabrics, nonwoven webs, porous foams, reticulated foams and the like, so long as the permeability of such liner material can be matched to or coordinated with the permeability of the subjacent layer of the absorbent structure to achieve the required improvement in liquid intake performance described herein. Nonwoven materials have been found particularly suitable for use in forming the bodyside liner of the present invention, including spunbond or meltblown webs of polyolefin filaments, or bonded carded webs of natural (for example, wood or cotton fibers) and/or synthetic (for example, polypropylene or polyester) fibers. For example, in the embodiment shown, bodyside liner 12 can be a nonwoven spunbond web of synthetic polypropylene filaments having a fiber size ranging from about 12 to about 48 microns, and more particularly from about 18 to about 43 microns. The nonwoven web can have a basis weight ranging from about 10.0 grams per square meter (gsm) to about 68.0 gsm, and more particularly from about 14.0 gsm to about 42.0 gsm, a bulk or thickness ranging from about 0.13 millimeter (mm) to about 1.0 mm, and more particularly from about 0.18 mm to about 0.55 mm, and a density between about 0.025 grams per cubic centimeter (g/cc) and about 0.12 g/cc, and more particularly between about 0.068 g/cc and about 0.083 g/cc. Additionally, the permeability of such nonwoven web can be from about 150 darcy to about 5000 darcy, and more particularly from about 850 darcy to about 1800 darcy, when measured in accordance with the test procedure described hereinbelow. The nonwoven web can be surface treated with a selected amount of surfactant, such as about 0.28% Triton X-102 surfactant, or otherwise processed to impart the desired level of wettability and hydrophilicity. It is considered desirable for purposes of the present invention for the nonwoven or other material utilized as a liner 12 to have at least the same, or a greater, level or degree of wettability and hydrophilicity as the subjacent layer 16. If a surfactant is used, it can be applied to the web by any conventional means, such as spraying, printing, brush coating and the like.

As used herein, the terms "hydrophilic" or "hydrophilicity" refer to fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used in forming a fibrous nonwoven web such as, for example, a bodyside liner or surge layer, can be provided by a Cahn SFA-222 Surface Force Analyzer System. When measured with this system, fibers having contact angles less than 90° are designated "wettable" or hydrophilic, while fibers having contact angles greater than 90° are designated "nonwettable" or hydrophobic.

Outer cover 14 is typically formed of a thin thermoplastic film, such as polyethylene film, which is substantially impermeable to liquid. Outer cover 14 functions to prevent body exudates contained in absorbent structure 20 from wetting or soiling the wearers clothing, bedding, or other materials contacting the diaper 10. In the embodiment shown, for example, outer cover 14 can be a polyethylene film having an initial thickness of from about 0.5 mil (0.012 millimeter) to about 5.0 mil (0.12 millimeter). The polymer film outer cover may be embossed and/or matte finished to provide a more aesthetically pleasing appearance. Other alternative constructions for outer cover 14 include woven or nonwoven fibrous webs that have been constructed or treated to impart the desired level of liquid impermeability, or laminates formed of a woven or nonwoven fabric and thermoplastic film. Outer cover 14 may optionally be composed of a vapor or gas permeable, microporous "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability.

Referring again to FIG. 1, disposed between liner 12 and outer cover 14 is an absorbent structure 20, which includes a surge layer 16 and an absorbent core 18. Absorbent core 18 suitably can be formed of a blend of hydrophilic cellulosic woodpulp fluff fibers and highly absorbent gelling particles (e.g., superabsorbent). Absorbent core 18 is generally compressible, conformable, non-irritating to the wearer's skin, and capable of absorbing and retaining liquid body exudates. For purposes of this invention, absorbent core 18 can comprise a single, integral piece of material, or a plurality of individual separate pieces of material. The size and absorbent capacity of absorbent core 18 should be compatible with the size of the intended user and the liquid loading imparted by the intended use of the diaper 10.

Surge layer 16 serves to quickly collect and temporarily hold discharged liquids, to transport such liquids from the point of initial contact and spread the liquid to other parts of the surge layer, and then to eventually release such liquids into the absorbent core 18. The surge layer 16 is most typically interposed between and in intimate, liquid communicating contact with the bodyside liner and the absorbent core, although other additional layers may be incorporated into the overall product design if so desired. Such a layer of material subjacent the inner (unexposed) surface of bodyside liner 12, although referred to herein as a surge layer, may alternatively be called a distribution layer, transfer layer, transport layer, and the like. In the embodiment shown in FIG. 1, surge layer 16 is placed in intimate, liquid communicating contact with liner 12 and absorbent core 18, in order to provide effective transfer of liquid from liner 12 to surge layer 16, and then to absorbent core 18. To further enhance liquid transfer, it can be desirable to attach the upper and/or lower surfaces of surge layer 16 to liner 12 and absorbent core 18, respectively. Suitable conventional attachment techniques may be utilized, including without limitation, adhesive bonding (using water-based, solvent-based and thermally activated adhesives), thermal bonding, ultrasonic bonding, needling and pin aperturing, as well as combinations of the foregoing or other appropriate attachment methods. If, for example, surge layer 16 is adhesively bonded to the bodyside liner 12, the amount of adhesive add-on should be sufficient to provide the desired level(s) of bonding, without excessively restricting the flow of liquid from the liner into the surge layer.

Various woven fabrics and nonwoven webs can be used to construct surge layer 16. For example, surge layer 16 may be a nonwoven layer composed of a meltblown or spunbond web of polyolefin filaments. Surge layer 16 also can be a bonded carded web or an airlaid web composed of natural and/or synthetic fibers. The bonded carded web may, for example, be a powder bonded carded web, an infrared bonded carded web, or a through-air bonded carded web. The infrared and through-air bonded carded webs can optionally include a mixture or blend of different fibers, and the fiber lengths within a selected web may range from about 6 mm to about 60 mm. The surge layer may be composed of a substantially hydrophobic material, and the hydrophobic material may optionally be treated with a surfactant or otherwise processed to impart a desired level of wettability and hydrophilicity. Surge layer 16 can have a generally uniform thickness and cross-sectional area.

Elastic members 25 may optionally be disposed adjacent each longitudinal edge 22 of diaper 10. Such elastic members are arranged to draw and hold the lateral, side margins 22 of diaper 10 against the legs of the wearer. Additionally, elastic members 27 also may be disposed adjacent either or both of the end edges 24 of diaper 10 to provide an elasticized waistband 32.

Diaper 10 may further include optional containment or barrier flaps (not shown) made from or attached to bodyside liner 12. Suitable constructions and arrangements for such containment flaps are described, for example, in U.S. Pat. No. 4,704,116, to K. Enloe, the disclosure of which is incorporated herein by reference to the extent that it is consistent herewith.

To secure the diaper 10 about the wearer, the diaper will have some type of fastening means attached thereto. As shown in FIG. 1, the fastening means can be adhesive tape tabs 28 attached to the inner and/or outer surface of outer cover 14 in the back waistband region of diaper 10. One or more plastic film strips or patches (not shown), sometimes referred to as a tape landing zone, may be attached to the outer surface of outer cover 14 in the front waistband region of diaper 10 to facilitate securement of the diaper 10 about the wearer's waist. Alternatively, various other fastening means, such as mechanical fasteners, hook-and-loop fasteners, and the like can be employed.

The above-described components of diaper 10 may be assembled together in a variety of well-known diaper configurations and using a variety of conventional techniques known in the art. For example, the components may be attached to one another using thermal or ultrasonic bonding, adhesives, such as hot melt pressure-sensitive adhesives, and the like, as well as combinations of the foregoing or other appropriate attachment means. In means. In the case of adhesive bonding, the adhesive can be applied using conventional methods, such as by spraying droplets or filaments of adhesive.

Referring again to bodyside liner 12, nonwoven webs that can be employed as liner 12 of the present invention can be formed by a variety of known forming processes, including spunbonding, airlaying, or bonded carded web formation processes. Spunbond nonwoven webs are made from melt-spun filaments. As used herein, the term "melt-spun filaments" refers to small diameter fibers and/or filaments which are formed by extruding a molten thermoplastic material as filaments from a plurality of fine, usually circular, capillaries of a spinnerette with the diameter of the extruded filaments then being rapidly reduced, for example, by non-eductive or eductive fluid-drawing or other well known spunbonding mechanisms. The production of spunbond nonwoven webs is described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,276,944 to Levy, U.S. Pat. No. 3,502,538 to Peterson, and U.S. Pat. No. 3,542,615 to Dobo et al., all of which are incorporated herein by reference.

Figure 2:
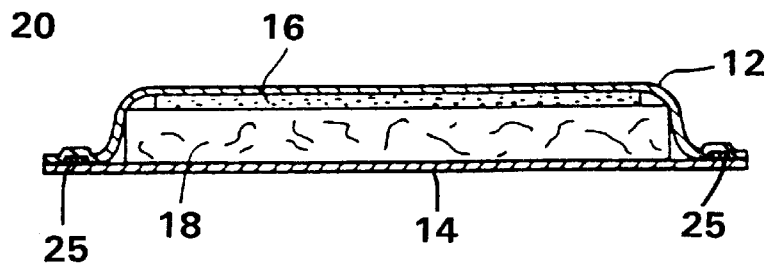
FIG. 2 is a cross-sectional view of the disposable diaper of FIG. 1.

In making the specific embodiment of the present invention shown in FIGS. 1 and 2, a conventional spunbond process is used to form a nonwoven web of melt-spun filaments formed from an extrudable thermoplastic resin. For example, an extrudable thermoplastic resin of about 98 percent polypropylene homopolymer and about 2 percent titanium dioxide has been found to work well in the present invention.

Figure 3:
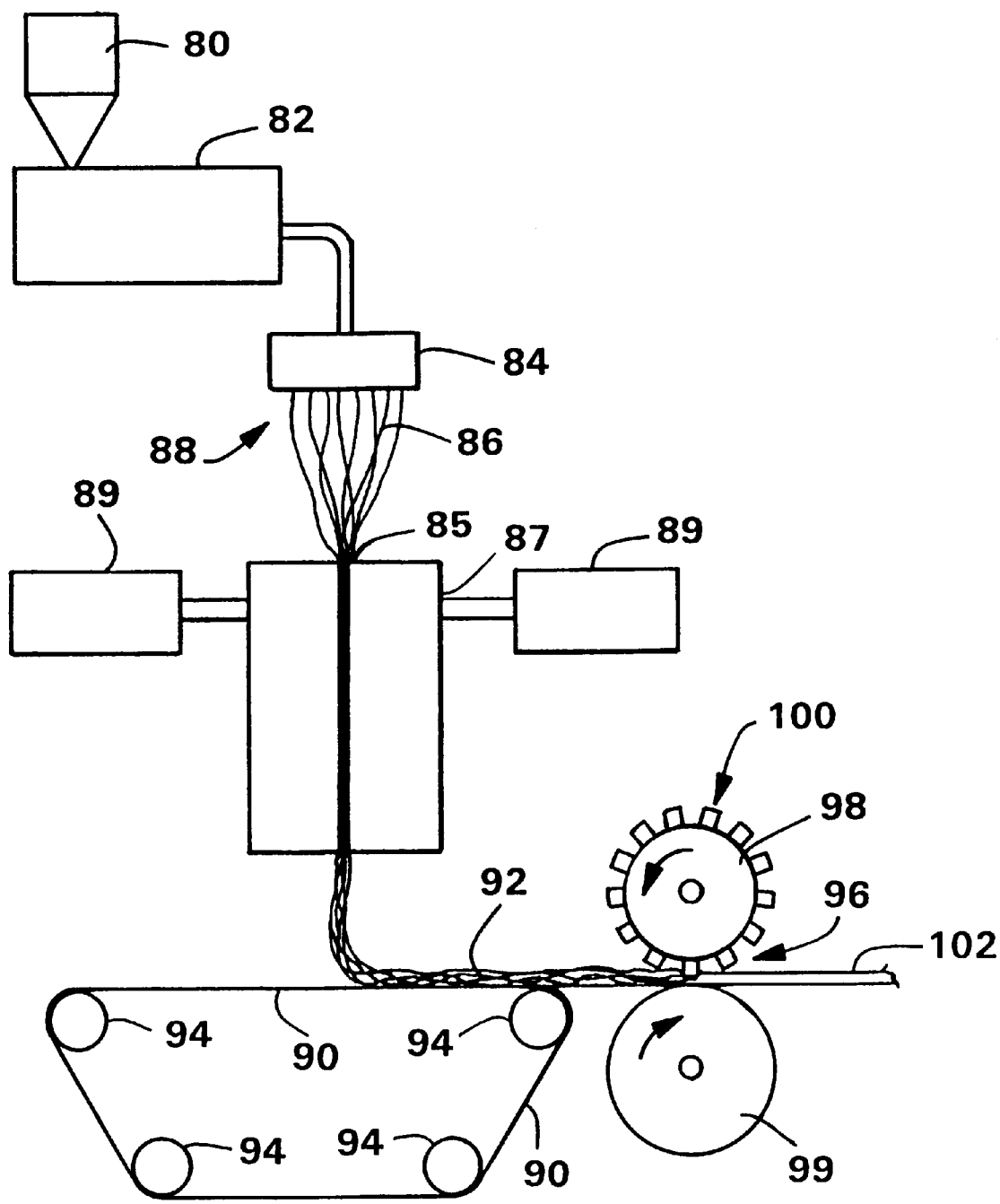
FIG. 3 is a schematic side view of a process and apparatus for producing a nonwoven web of melt-spun filaments.

A suitable spunbond process and apparatus for producing a nonwoven web of melt-spun polymer filaments are schematically illustrated in FIG. 3. In forming such a nonwoven web of melt-spun polymer filaments (e.g., spunbonded filaments), pellets, chips or the like of a polymer material are introduced into a pellet hopper 80 of an extruder 82. The extruder 82 has an extrusion screw (not shown) that is driven by a conventional drive motor (not shown). As the polymer advances through the extruder 82, due to rotation of the extrusion screw by the drive motor, the polymer is progressively heated to a molten state. Heating of the polymer to the molten state may be accomplished in a plurality of discrete steps with its temperature being gradually elevated as it advances through discrete heating zones of the extruder 82 toward an extrusion die 84. The die 84 may be yet another heating zone where the temperature of the polymer is maintained at an elevated level for extrusion. The temperature which will be required to heat the polymer to a molten state will vary somewhat depending upon the type of polymer used. For example, polypropylene may be extruded at a temperature of from about 200° C. to about 270° C. Heating of the various zones of the extruder 82 and the extrusion die 84 may be achieved by any of a variety of conventional heating arrangements (not shown).

The filaments of the molten polymer are initially formed and discharged in a filament curtain or stream 86 from spaced-apart filament forming means. The forming means 88 may be any suitable filament forming means, such as spinnerettes, die orifices, or similar equipment associated with melt-spinning processes such as, for example, the spunbonding process. The spun filaments discharged from the forming means 88 are drawn through passage 85 in fiber draw unit 87, to which high speed fluid sources 89, such as jet streams of air, are operatively connected. The action of the high speed fluid on the melt-spun filaments 86 passing downwardly through passage 85 stretches the melt-spun filaments 86, and increases the speed of delivery of the melt-spun filaments to a forming surface 90. The melt-spun filaments upon exiting passage 85 are deposited in a random manner on a foraminous forming surface 90, generally assisted by a vacuum device (not shown) placed underneath the forming surface 90. The purpose of the vacuum is to eliminate the undesirable scattering of the filaments and to guide the filaments onto the forming surface 90 to form a nonwoven web 92 of melt-spun polymer filaments. The forming surface 90 is supported in turn on roller 94 driven by conventional drive means (not shown).

The nonwoven web 92 separates from the forming surface 90, and is directed into and through nip 96 of a patterned roller arrangement 100. The pattern roll 98 is used for thermal bonding of the web 92. The smooth anvil roll 99, together with the pattern roll 98, defines a thermal pattern bonding nip 96. Alternatively, anvil roll 99 also may bear a bonding pattern on its outer surface. The pattern roll 98 is heated to a suitable bonding temperature by heating means (not shown) and is rotated by conventional drive means (not shown), so that when the web 92 passes through nip 96, a series of thermal pattern bonds is formed. As a result of the thermal pattern bonding, the web 92 of filaments becomes a pattern bonded web 102 of enhanced stability. In the spunbond apparatus illustrated in FIG. 3, the pattern roll 98 has a point bond pattern with a surface bond area of from about 10 percent to about 25 percent or more, using a bond point density of from about 15.5 to about 46.5 bond points per square centimeter ($cm^2$). Bond densities above and below this range also can be used, with the specific bond density being dependent upon the size of the individual bond points. The pattern bonded web 102 then is passed to other process and/or treatment steps.

The spunbond process also can be used to form bicomponent spunbond nonwoven webs as, for example, from side-by-side or sheath/core polyethylene/polypropylene spunbond bicomponent filaments. A suitable process for forming such bicomponent spunbond nonwoven webs is described in U.S. Pat. No. 5,418,045 to Pike et al., which is incorporated herein by reference in its entirety. This process for forming such filaments and resultant webs includes using a pair of extruders for separately supplying the polymer components to a bicomponent spinnerette. Spinnerettes for producing bicomponent filaments are well known in the art and, therefore, are not described herein in detail. Generally, the spinnerette includes a housing containing a spin pack, which includes a plurality of vertically stacked plates having a pattern of openings arranged to create flow paths for directing the high melting temperature and low melting temperature polymers separately to the fiber-forming openings in the spinnerette. The spinnerette has openings arranged in one or more rows and the openings form a downwardly extending curtain of filaments when the polymers are extruded through the spinnerette. As the curtain of filaments exit the spinnerette, they are contacted by a quenching gas from one or both sides of the filament curtain, which at least partially quenches the filaments and develops a latent helical crimp in the filaments extending from the spinnerette. Typically, the quenching air will be directed generally perpendicularly to the length of the filaments at a velocity of from about 30 to about 120 meters per minute and at a temperature of about 7° C. to about 32° C.

A fiber draw unit or aspirator is positioned below the quenching gas to receive the quenched filaments. Fiber draw units or aspirators for use in melt spinning polymers are well known in the art, as noted above. Exemplary fiber draw units suitable for use in the this process include a linear fiber aspirator of the type shown in U.S. Pat. No. 3,802,817 to Matsuki et al., and eductive guns of the type shown in U.S. Pat. No. 3,692,618 to Dorschner et al. and U.S. Pat. No. 3,423,266 to Davies et al., the disclosures of which are incorporated herein by reference in their entirety. The fiber draw unit in general has an elongated passage through which the filaments are drawn by aspirating gas flowing through the passage. The aspirating gas may be any gas, such as air, that does not adversely interact with the polymers of the filaments. A heater supplies hot aspirating gas to the fiber draw unit. As the aspirating gas draws the quenched filaments and ambient air through the fiber draw unit, the filaments are heated to a temperature that is required to activate the latent crimping therein. The temperature required to activate the latent crimping within the filaments will range from about 43° C. to a maximum of less than the melting point of the low melting component polymer. Generally, a higher air temperature produces a higher number of crimps per unit length of the filament.

The drawn and crimped filaments exit the fiber draw unit and are deposited onto a continuous forming surface in a random matter, generally assisted by a vacuum device placed underneath the forming surface. The purpose of the vacuum is to eliminate the undesirable scattering of the filaments and to guide the filaments onto the forming surface to form a uniform unbonded nonwoven web of bicomponent filaments. If desired, the resultant web can be lightly compressed by a compression roller or other suitable means in increase web structural integrity before the web is subjected to a bonding process.

One method for bonding the bicomponent spunbonded web employs a through-air bonder. Such through-air bonders are well known in the art and, therefore, through-air-bonding is only generally described hereinbelow. Another method for bonding bicomponent spunbond nonwoven webs is thermal point bonding, which is well known to those skilled in the art and need not be described herein in detail. A suitable thermal bonding process is described in U.S. Pat. No. 3,855,046 to Hansen, et al., the disclosure of which is incorporated herein by reference in its entirety. Other bonding processes for bonding bicomponent spunbond nonwoven webs may also be utilized, such as adhesive bonding, oven bonding, ultrasonic bonding, or hydroentangling, or combinations thereof. Such bonding techniques likewise are well known to those of ordinary skill in the art and are not discussed in detail herein.

Bodyside liner 12 also may be made from bonded carded webs. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding, as discussed hereinbelow.

Airlaying is another well known process by which fibrous nonwoven layer 12 can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

Surge layer 16 also can suitably be formed of a nonwoven material, formed in any of the above-described manners. It has been found that an effective nonwoven web for constructing surge layer 16 can be characterized by certain specific parameters. Such parameters include, for example, basis weight, bulk, bulk recovery, density, permeability, and surface area per void volume (SA/VV). Further parameters can include a bonding matrix which will help stabilize the pore size structure, and hydrophilicity. The bond matrix and the blend of fiber deniers can advantageously provide for and substantially maintain a desired pore size structure. In addition, utilization of bicomponent fibers, such as polyethylene sheath/polyester core fibers, in forming surge layer 16 may yield advantageous results. Such bicomponent fibers may be flat crimped or helically crimped, as is known in the art.

For example, in the embodiment shown in FIG. 1, surge layer 16 can be a bonded, carded, single layer fibrous web formed of a homogeneous blend of bicomponent fibers and natural and/or synthetic staple fibers. Surge layer 16 can have a basis weight of at least about 0.50 ounce per square yard (about 17 grams per square meter), a density of at least about 0.010 gram per cubic centimeter at a pressure of 68.9 pascals, a bulk of at least about 1.0 mm at a pressure of 68.9 pascals, a bulk recovery of at least about 75 percent, a permeability of about 500 to about 5000 darcy, and a surface area per void volume of at least about 20 square centimeters per cubic centimeter.

Through-air-bonding is considered to be a particularly suitable method for bonding such nonwoven webs formed of or incorporating bicomponent fibers. Such through-air bonders are well known in the art and need not be described in detail herein. Generally, the through-air bonder includes a perforated roller, which receives the web, and a hood surrounding the perforated roller. A flow of heated air is directed from the hood and applied through the web and into the perforated roller. The heated air heats the web to a temperature above the melting point of the lower melting point component of the bicomponent fibers, but below the melting point of the higher melting point component. Upon heating, the lower melting polymer portions of the web fibers melt and adhere to adjacent fibers at their cross-over points, while the higher melting polymer portions of the fibers tend to maintain the physical and dimensional integrity of the web. When polyethylene and polyester are used as the polymer components, for example, the air flowing through the through-air bonder can have a temperature ranging from about 110° C. to about 140° C. and a velocity from about 10 to about 150 meters per minute. The dwell time of the web in the through-air bonder typically should not exceed about 6 seconds. It should be understood, however, that the parameters of the through-air bonder depend on factors such as the type of polymers used, the thickness of the web, web line speed, etc.

The inventors consider appropriately matching or correlating the permeability of the liner to that of the subjacent surge layer critical to obtaining the improvements in liquid intake performance described herein. Thus, the present invention is generally directed to placing a liner material having a first permeability in liquid communicating contact with a subjacent layer, such as a surge layer, having a second permeability, such that the liquid-runoff performance of the liner/subjacent layer combination is improved by at least 50 percent over the liquid-runoff performance of the subjacent layer alone, when measured in accordance with the test procedure described hereinbelow (i.e., the amount of run-off liquid from the liner/subjacent layer combination is no more than about half of the amount of run-off liquid from the subjacent layer alone). Accordingly, as used herein, the term "matched permeability" refers to the permeability of a liner material and the permeability of a subjacent layer, which when appropriately set as disclosed herein the above-described liquid intake performance improvement is achieved when the liner and subjacent layer are placed in liquid communicating contact and insulted with liquid.

Alternatively, the present invention can be described by characterizing the permeability of the liner as falling within a specified range of the permeability of the subjacent layer, expressed as a percentage of the permeability of the subjacent layer. Thus, in accordance with the teachings of the present invention, the permeability of the liner should be within about 55 percent to about 120 percent of the permeability of the subjacent layer. In another suitable embodiment of the present invention, the liner has a permeability within about 85 percent to about 110 percent of the permeability of the subjacent layer.

Having described the above embodiments of the present invention, a series of examples of matched permeability liner/absorbent structure systems are provided to further illustrate this invention. These samples were be tested to determine permeability and liquid run-off and run-through, using the test methods set forth below.

TEST PROCEDURES

Basis Weight

The basis weight for each of the samples is determined in accordance with Federal Test Method 191A/5041. Sample sizes are 9 inches by 9 inches (22.9 centimeters by 22.9 centimeters) and a total of 8 samples are weighed and then are averaged for each material. The values reported are for the average.

Liner Layer Bulk (Thickness)

The bulk of the liner materials, which is a measure of thickness, is measured at 0.5 psi with a Starret-type bulk tester.

Surge Layer Bulk (Thickness) and Bulk Recovery

Bulk and bulk recovery of a surge layer can be measured using an INSTRON or SINTECH tensile tester to measure the resisting force as a material is compressed between a movable platen and a fixed base at a constant rate using a certain amount of force and subsequently releasing the force at the same rate. Preferably pressure, or force, and the platen pressure are recorded. If only force is recorded, pressure is calculated using the equation:

$$P_{reading} = \frac{F \times 10,000 \text{ cm}^2 / \text{m}^2}{A_p}$$

where:

$P_{reading}$=pressure reading from the SINTECH or INSTRON in pascals

F=force pushing back on the platen in pascals $A_p$=area of the platen in square centimeters (19.02 cm$^2$)

In performing the measurements, the base of the apparatus must be larger in size that the platen. Zero height between platen and base distance is set by bringing the platen down until it barely touches the base. The platen then is raised to the desired initial height from zero distance. The initial platen position must be greater than the initial thickness of the material so that the test starts out at zero pressure on the sample. The material can be the same size as the platen or larger.

A 4.92 centimeter diameter circular platen is used to compress materials against the fixed base at a rate of 5.00 mm/minute up to a maximum load of 13,790 pascals (2.0 psi). The platen then is returned at the same rate to the initial starting position. The initial starting position for the platen is 13 millimeters from the base. Material samples are cut to 10.16 centimeter square shapes and tested in the center of the samples. Force and position data are recorded every 0.01 minutes or every 0.5 millimeters. Three samples are run for each material and averaged. The values reported would be for the averages. The same is also true for bulk recovery values.

Suitable equipment for this test could include:

Compression Tester

INSTRON model 6021 with compression test software and 1 kN load cell made by INSTRON of Bucks, England.

Balance

Mettler model PM4600 of Highstown, N.J.

To measure bulk or thickness, the following equation is used:

Bulk(thickness)=$X_o$-X where:

$X_o$=distance of initial platen position from the base in millimeters

X=platen position from initial position in millimeters at a specific pressure, in this case 68.9 pascals Thus, all bulk values reported would be for sample surge materials while under a load or pressure of 68.9 pascals.

Percent Bulk Recovery in the dry state for the sample materials is calculated at 68.9 pascals (0.01 pounds per square inch) using the platen positions on the compression and recovery cycles when the pressure on the sample is 68.9 pascals. The formula to be used is as follows:

$$\% \text{ Bulk Recovery} = \frac{\text{Recovered Bulk at 68.9 pascals}}{\text{Initial Bulk at 68.9 pascals}} \times 100$$

Density

The density of the materials is calculated by dividing the weight per unit area of a sample in grams per square meter (gsm) by the bulk of the sample in millimeters (mm) at 68.9 pascals and multiplying the result by 0.001 to convert the value to grams per cubic centimeter (g/cc). A total of three samples would be evaluated and averaged for the density values.

Surface Area Per Void Volume (SA/VV)

Surface area per void volume is calculated by determining the fiber surface area in square centimeters per one gram of sample and dividing that by the void volume of the sample, which is simply the inverse of density measured at 68.9 pascals. Surface area per void volume gives an indication of how much resistance liquid encounters as it passes through the web structure. SA/VV can be thought of as being similar to the mesh size of a screen. A large SA/VV means that the wires of the screen are closer together, thus making the holes in the screen smaller. As the holes get smaller, it becomes more difficult for liquid to pass through the screen. For purposes of the functionality of surge layers, it can be desirable to utilize webs with low SA/VV values so that liquid can pass through the web with relative ease. The data generated from the procedure would be based upon an average of three measurements per sample.

The surface area of the fibers in a one gram sample of web material is calculated using the following equation:

Surface Area (SA) per gram of web=3363×{(Fiber 1 Denier/Fiber 1 Density)$^{0.5}$×(1/Fiber 1Denier)×Fiber 1 Weight % of Web}+3363×{(Fiber 2 Denier/Fiber 2 Density)$^{0.5}$×(1/Fiber 2 Denier)×Fiber 2 Weight % of Web}.

Surface Area per Void Volume (SA/VV) then is calculated by dividing the SA by the VV or, as stated above, multiplying by the density of the web as follows:

SA/VV=SA (cm$^2$/g)×Density of Web (g/cm$^3$)=SA/VV in cm$^2$/cm$^3$.

MD Tensile Strength

The machine direction (MD) tensile strength of a sample surge layer is measured in accordance with ASTM D 5035-90 test method, except that sample sizes will be 7.6 centimeters by 15.2 centimeters with the machine direction of the sample running in a direction parallel to the longer dimension of the sample. A total of eight sample materials are tested and then averaged. The values reported would be for the averages.

Permeability Test

Permeability indicates the ease or difficulty with which a fluid flows through a structure when a pressure gradient is applied to a fluid. The resulting fluid velocity through the structure is controlled by the permeability of the structure. The permeability of sample materials in the Z-direction, which is through the thickness of the material, is measured by a forced flow test, which is described in detail in an article by Bernard Miller and David B. Clark entitled, "Liquid Transport Through Fabrics; Wetting and Steady-State Flow" published in *Textile Research Journal*, pages 150 through 155, (March 1978). The foregoing article is incorporated herein by reference in its entirety.

To perform the test, a forced flow resistance monitor is built in accordance with the instructions in the foregoing article. In the forced flow test, the sample is held in a cylinder and fluid is pushed through the material at a constant velocity by a piston and the back pressure against the piston is recorded. The permeability is calculated using Darcy's Law which describes fluid flow through a porous medium according to the following equation:

$$v = \frac{Q}{A} = -\frac{k_z}{\mu} \cdot \frac{dp}{dz}$$

where:

v=superficial flow velocity or piston velocity in centimeters per minute

Q=volume flow rate in cubic centimeters per second

A=cross sectional area of the inner diameter of the tube (31.7 square centimeters)

$k_z$=material permeability constant z=thickness in centimeters of the material dp/dz=pressure gradient across the material in Pascals per centimeter $\mu$=fluid viscosity (cp) which is about 6 cp for Penetek oil This equation can in turn be solved for permeability in the Z-direction ($k_z$) in the units of darcy as follows:

$$k_z = \frac{v \cdot m}{\frac{dp}{dz}} \cdot \frac{0.001 \text{ Pa} \cdot \text{sec/cp}}{60 \text{ sec/min}} \cdot 1.032 \times 10^8 \text{ darcy/cm}^2$$

The pressure drop for the test is obtained using a computer software program which measures the pressure vs. time. The pressure drop is equal to the change in pressure between the pause point and when the piston starts up again.

The thickness of the material is obtained by exerting a 0.05 pound per square inch (psi) load on to the sample with a 3 inch (76.2 mm) circular acrylic platen which is attached to a DIGIMATIC INDICATOR Type 543-445-1 Model ID 1050ME, available from Mitutoyo Mfg. Co. Ltd. of Japan.

The equipment used in conjunction with the test apparatus includes a pressure transducer Model #264 from SETRA Systems of Acton, Mass. This pressure transducer is capable of measuring up to 25 inches of water pressure. The additional equipment to be used includes a chart recorder Model SE 120, 881221100 from BBC Goerz Metrawatt of Austria; a slide and motor positioner model #B4036W1J from Velmex, Inc. of Holcomb, N.Y.; a stepper motor controller model #14V 8K BASIC from Centroid Corporation of State College, Pa.; and, a COMPAQ® personal computer with a serial port.

Calibration of the pressure measurements is accomplished by adding a known weight or volume of fluid to the cylinder and comparing the pressure transducer response to the theoretical pressure increase using the formula:

$$DP_{theory} = r \cdot g \cdot h = g \cdot M/A \cdot 100 \text{ cm/m} \cdot 0.001 \text{ kg/gram}$$

where:

D $P_{theory}$=theoretical pressure change in Pascals r=fluid density in grams per cubic centimeter g=standard acceleration of gravity which is 981 centimeters per square second h=height of fluid added to cylinder in centimeters A=inner area of cylinder in square centimeters which is 31.7 square centimeters M=fluid mass in grams In deriving the permeability data, no screens are used to hold the samples in place. Instead, two halves of a 6.35 cm inner diameter cylinder which screwed together with a 7.62 cm diameter sample positioned between the two cylinder pieces. Mineral oil is used as the fluid. Specifically, the mineral oil is Penetek technical grade mineral oil from Penreco of Los Angeles, Calif. The mineral oil has a viscosity of approximately 6 centipoise. The piston velocity is 20 cm/min. The results of this procedure would be reported in units of darcy.

Liquid Run-Off and Run-Through Test

This test measures the amount of liquid that penetrates one or more liquid-permeable materials, such as a bodyside liner and/or surge layer. A schematic illustration of the apparatus to be employed in performing this test is shown in FIG. 4.

To conduct this test, the test sample 40 is placed over a 3 inch×3 inch (76.2×76.2 mm) opening 45 in sample holder 44. Sample holder 44 includes suitable means for holding the test sample 40 in place over the opening 45, such as clips (not shown). The clips are situated on three sides of opening 45. The dimensions of sample 40 should be sufficient to completely cover opening 45 and extend into at least one of the clips. Sample sizes for the liner materials are 4 inches by 8 inches (101.6 mm by 203.2 mm). Samples sizes for the surge materials would be 2 inches by 6 inches (50.8 mm by 152.4 mm).

Figure 4:
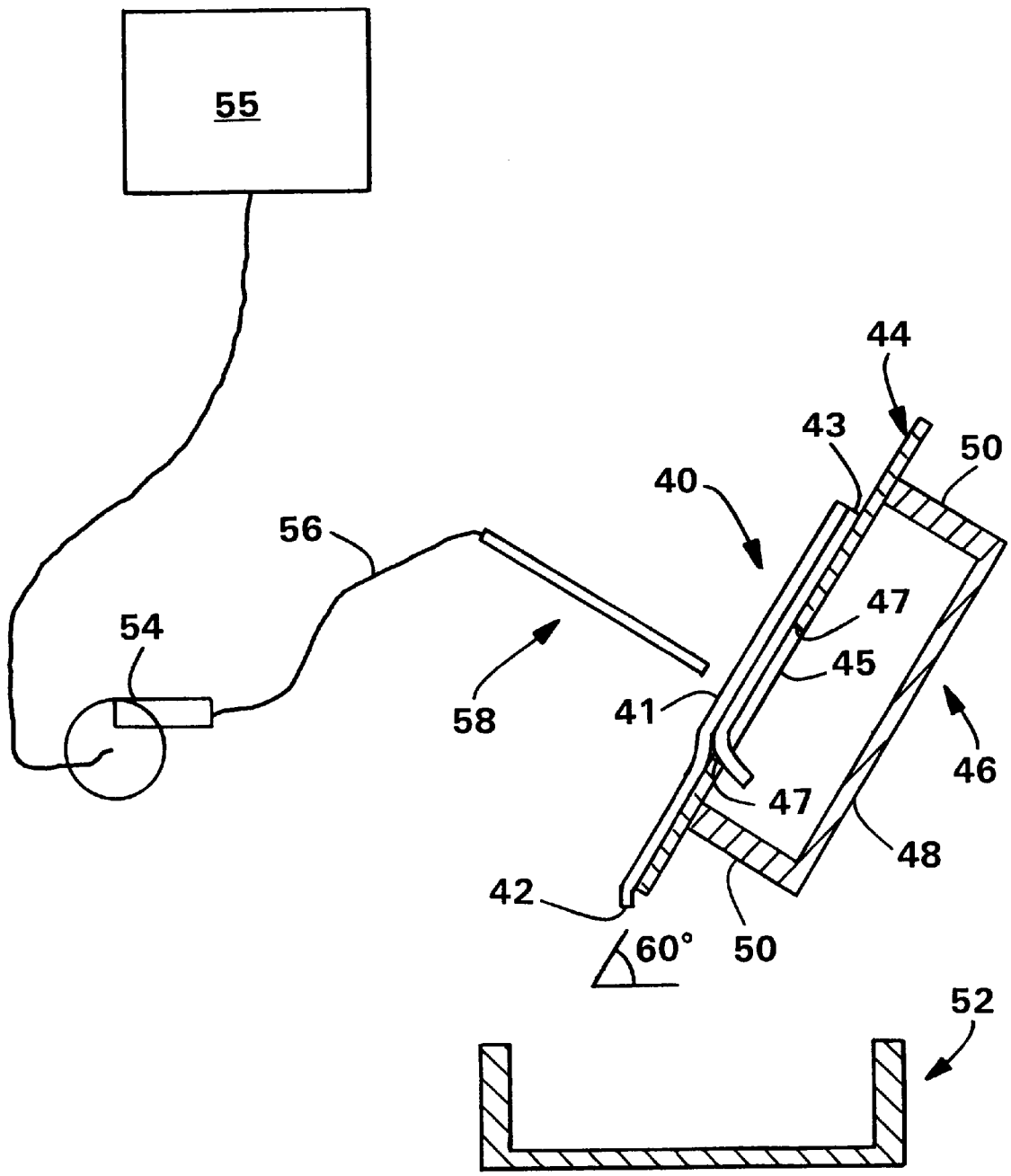
FIG. 4 is a schematic side view of a testing apparatus that can be used in conducting the Run-Off and Run-Through Test procedure described herein.

As shown in FIG. 4, when test sample 40 includes two layers of material, the bottom layer of material 43 (which in all two-layer Examples is a surge layer) is attached on its upper end with a clip. The lower end of the bottom layer 43, which is not held by a clip, is placed through opening 45 in sample holder 44 and the top surface of the bottom layer 43 is attached to side wall 47 of opening 45 using conventional means, such as double-sided adhesive tape. The upper layer of material 42 (which in all two-layer Examples is a liner layer) then is placed over the bottom layer 43 and secured on three sides by the clips, including the clip holding the bottom layer 43 in place. The free lower end of the upper layer 42 not secured within a clip is not, however, inserted through opening 45. Rather, the bottom surface of this free end of upper layer 42 is attached to the lower end of sample holder 44 using conventional means, such as double-sided adhesive tape.

When test sample 40 is a single layer of material (not shown), the end of sample 40 that is not held by a clip is attached to the lower end of sample holder 44. This configuration is intended to ensure that only test liquid that runs through sample 40 enters first container 46 for collection and measurement. First container 46 is formed of any suitable material that is capable of containing the test liquid that is injected into the test sample 40. Likewise, the dimensions of first container 46 need to be sufficient to contain the amount of test liquid that is injected into and runs through the sample 40. For example, as shown in FIG. 4, first container 46 is formed of clear PLEXIGLAS® and has a 152.4 mm×152.4 mm base 48 and 76.2 mm high side walls 50.

Once test sample 40 is properly situated on sample holder 44, holder 44 is placed over the opening in first container 46 formed by the side walls 50. Then, holder 44 and first container 46 are oriented at an insult angle of 60o measured from the horizontal. A second container 52 is positioned beneath first container 46 to collect any run-off test liquid that does not penetrate, and is not absorbed by, test sample 40. Second container 52 may be identical in construction to first container 46, however, no sample holder 44 is placed over second container 52.

A conventional pump 54, such as a Masterflex Pump Model 7526-00 available from Cole Palmer Instrument Co. of Barrington, Ill., is adjusted to deliver 100 milliliters (ml) of a test liquid 55 at a rate of 10 milliliters per second (ml/sec) through flexible tubing 56, such as Masterflex tubing part number 6424-17 available from Cole Palmer Instrument Co., to an insult nozzle 58. The test liquid 55 employed is Baxter Blood Bank Saline, Catalog No. b3158-1, or its equivalent. Nozzle 58, which has a discharge diameter of 0.150 inch (3.810 mm), is oriented perpendicularly to the exposed, top surface 41 of sample 40 at a distance of about 0.25 inch (6.35 mm) from top surface 41.

Pump 54 is activated to inject a single insult of 100 ml of saline into sample 40. The amount of saline collected in first container 46 and second container 52 is measured. Liquid collected in first container 46 is called run-through and liquid collected in second container 52 is called run-off. Liquid retained in the sample is called retained liquid. Low values for run-off and retained liquid and high values for run-through are considered advantageous for liner materials suitable for use in absorbent articles.

EXAMPLES

A total of six sample liner materials and one surge material are set forth in the following Tables. In these Tables, the nonwoven webs identified as liners were formed of spunbonded filaments made using a pilot-scale apparatus, essentially as described in U.S. Pat. No. 3,802,817 to Matsuki et al. The spunbonded filaments were formed from an extrudable thermoplastic resin which contained about 98 percent, by weight, of polypropylene homopolymer, and about 2 percent titanium dioxide. The polypropylene homopolymer used was obtained from Exxon having offices in Houston, Tex., under the product designation 3445. The spunbonded filaments were essentially continuous in nature and had an average fiber size as indicated in Table I below. The spunbond nonwoven webs were thermally point-bonded with a percent bond area of about 15 percent. The spunbond nonwoven webs were hand-treated for wettability using Triton X-102 at a 0.25 percent add-on level.

In the Tables below, the nonwoven web identified as a surge was formed from a uniformly mixed blend of 90 weight percent 3.0 denier Merge 1039 polyethylene/polyester sheath/core fibers from BASF Corporation of Enka, N.C. and 10 weight percent of 1.5 denier rayon fibers Merge 18453 from Courtaulds Fibers Incorporated of Axis, Alabama. Thw web was bonded in a through air dryer at a line speed of 15 meters per minute at a temperature of 135° C. and at an air flow hood pressure of 423 pascals. The dwell time within the dryer per unit area of web materials was 1.6 seconds. The resultant web had a bulk at 68.9 pascals of 3.53 mm, a bulk recovery of 86 percent, a density of 0.031 g/cc at 68.9 pascals, a surface area per void volumer of 57.1 $cm^2/cm^3$ at 69.9 pascals, and a permeability of 1545 Darcy, when measured in accordance with the test procedure described herein.

The above-described sample materials have the following properties:

TABLE I

| EXAMPLE | FIBER SIZE (Denier) | BULK (mm) | BASIS WEIGHT (g/m$^2$) | DENSITY (g/cc) |
|---|---|---|---|---|
| LINER A | 2 | 0.241 | 20 | 0.083 |
| LINER B | 3.5 | 0.254 | 20 | 0.079 |
| LINER C | 5 | 0.286 | 20 | 0.070 |
| LINER D | 10.5 | 0.551 | 42 | 0.076 |
| LINER E | 12 | 0.546 | 42 | 0.077 |
| LINER F | 7 | 0.323 | 22 | 0.068 |

TABLE II

| EXAMPLE | PERMEABILITY (Darcy) | COEFFICIENT OF VARIATION (%) | NUMBER OF MEASUREMENTS |
|---|---|---|---|
| COMPARATIVE LINER A | 310 | 21 | 4 |
| COMPARATIVE LINER B | 530 | 18 | 6 |
| LINER C | 850 | 15 | 4 |
| LINER D | 1338 | 10 | 3 |
| LINER E | 1581 | 16 | 4 |
| LINER F | 1771 | 16 | 5 |
| SURGE | 1545 | 7 | 7 |

TABLE III

| EXAMPLE | LIQUID RUN-OFF (ml) | STANDARD DEVIATION | COEFFICIENT OF VARIATION (%) | NUMBER OF MEASUREMENTS |
|---|---|---|---|---|
| COMPARATIVE LINER A | 94.0 | 5.0 | 5.3 | 16 |
| COMPARATIVE LINER B | 75.0 | 19.2 | 25.6 | 18 |
| LINER C | 43.5 | 11.6 | 26.6 | 20 |
| LINER D | 37.9 | 11.3 | 29.9 | 20 |
| LINER E | 36.9 | 10.7 | 29.0 | 15 |
| LINER F | 19.0 | 9.6 | 50.7 | 18 |

TABLE IV

| EXAMPLE | LIQUID RUN-OFF (ml) | STANDARD DEVIATION | COEFFICIENT OF VARIATION (%) | NUMBER OF MEASUREMENTS |
|---|---|---|---|---|
| SURGE WITH: | | | | |
| COMPARATIVE LINER A | 52 | 20.4 | 39.5 | 20 |
| COMPARATIVE LINER B | 23 | 13 | 56.4 | 30 |
| LINER C | 19 | 9.8 | 51.4 | 30 |
| LINER D | 15.3 | 8.6 | 56.6 | 25 |
| LINER E | 16 | 6.4 | 40.1 | 30 |
| LINER F | 17.4 | 9.5 | 54.5 | 30 |
| SURGE ALONE | 46.3 | 6.4 | 13.8 | 16 |

Upon combining the liner samples of Table III with the surge material of Table II having a permeability of about 1545 darcy, and subjecting the liner/surge combination to the Run-Off and Run-Through Test described above, it can be seen that the permeabilities of Liners C through F constitute a match with that of the surge material, and thus fall within the scope of the present invention. Table IV shows the runoff amounts from a combination 10 of the about 1545 darcy surge with each liner and of the surge alone. As shown in Table IV, such matched liner/surge combinations exhibit the requisite improvement in liquid run-off performance of at least about 50 percent over that of the surge alone, with liquid run-off amounts for these liner/surge combinations ranging from about 15.0 milliliters (ml) to about 17.0 ml. It is further shown that Liners D and E, which most closely match the about 1545 darcy permeability of the surge layer, exhibit the greatest improvement in liquid run-off performance of the liner materials identified above. Based upon the foregoing examples, it can readily be seen that the inventors have provided a matched permeability liner/absorbent structure system that achieves significantly improved liquid intake performance.

It is contemplated that the matched permeability liner/absorbent structure system constructed in accordance with the present invention will be tailored and adjusted by those of ordinary skill in the art to accommodate various levels of performance demand imparted during actual use. Accordingly, while this invention has been described by reference to the above embodiments and examples, it will be understood that this invention is capable of further modifications. This application is, therefore, intended to cover any variations, uses or adaptations of this invention following the general principles thereof, and including such departures from the present disclosure as come within the known or customary practice in the art to which this invention pertains and fall within the limits of the appended claims.

What is claimed is:

1. A matched permeability liner/absorbent structure system comprising:
   a liner having a first permeability and first level of hydrophilicity;
   a subjacent nonwoven layer having a second permeability and second level of hydrophilicity;
   said liner being in liquid communicating contact with said subjacent layer;
   said subjacent layer having a liquid run-off amount;
   said liner and subjacent layer having a combined liquid run-off amount;
   wherein said combined liquid run-off amount is at least 50 percent less than said subjacent layer liquid run-off amounts said first permeability is within the range of about 85 percent to about 110 percent of said second permeability and wherein said first level of hydrophilicity is at least as great as said second level of hydrophilicity.

2. The matched permeability liner/absorbent structure system according to claim 1 wherein said liner is a nonwoven web.

3. The matched permeability liner/absorbent structure system according to claim 1 wherein said liner is a spunbond web.

4. The matched permeability liner/absorbent structure system according to claim 1 wherein said liner is a bonded carded web.

5. The matched permeability liner/absorbent structure system according to claim 1 wherein said subjacent layer includes bicomponent fibers.

6. The matched permeability liner/absorbent structure system according to claim 1 wherein said liner and said subjacent layer comprise polyolefins.

7. The matched permeability liner/absorbent structure system according to claim 1 wherein said liner and said subjacent layer are attached together.

8. The matched permeability liner/absorbent structure system according to claim 1 wherein said combined liquid run-off amount is at least about 65 percent less than said subjacent layer liquid run-off amount.

9. A matched permeability liner/absorbent structure system comprising:
   a liner having a first permeability and first level of hydrophilicity;
   a subjacent nonwoven layer having a second permeability and second level of hydrophilicity;
   said liner and said subjacent layer being in liquid communicating contact; and said first permeability is within the range of about 85 percent and about 110 percent of said second permeability and said first level of hydrophilicity is at least as great as said second level of hydrophilicity.

10. The matched permeability liner/absorbent structure system according to claim 9 wherein said liner is a nonwoven web.

11. The matched permeability liner/absorbent structure system according to claim 9 wherein said liner is a spunbond web.

12. The matched permeability liner/absorbent structure system according to claim 9 wherein said liner is a bonded carded web.

13. The matched permeability liner/absorbent structure system according to claim 9 wherein said subjacent layer includes bicomponent fibers.

14. The matched permeability liner/absorbent structure system according to claim 9 wherein said liner and said subjacent layer comprise polyolefins.

15. The matched permeability liner/absorbent structure system according to claim 9 wherein said liner and said subjacent layer are attached together.

16. The matched permeability liner/absorbent structure system according to claim 9 wherein:
    said subjacent layer has a liquid run-off amount;
    said liner and subjacent layer have a combined liquid run-off amount;

wherein said combined liquid run-off amount is at least 50 percent less than said subjacent layer liquid run-off amount.

17. The matched permeability liner/absorbent structure system according to claim 9 wherein said combined liquid run-off amount is at least 65 percent less than said subjacent layer liquid run-off amount.

18. A disposable absorbent article comprising:

a liner having a first permeability and first level of hydrophilicity;

an outer cover;

an absorbent structure disposed between said liner and said outer cover;

said absorbent structure comprising a subjacent nonwoven layer having a second permeability and second level of hydrophilicity and an absorbent core;

said liner being in liquid communicating contact with said subjacent layer;

said subjacent layer having a liquid run-off amount;

said liner and subjacent layer having a combined liquid run-off amount;

wherein said combined liquid run-off amount is at least 50 percent less than said subjacent layer liquid run-off amount, said first permeability is within the range of about 85 percent to about 110 percent of said second permeability and wherein said first level of hydrophilicity is at least as great as said second level of hydrophilicity.

19. The disposable absorbent article according to claim 18 wherein said combined liquid run-off amount is at least 65 percent less than said subjacent layer liquid run-off amount.

* * * * *